(12) United States Patent
Bäbler et al.

(10) Patent No.: US 6,901,811 B2
(45) Date of Patent: Jun. 7, 2005

(54) TEST DEVICE FOR FEMORAL HEAD PROSTHESIS

(75) Inventors: Jean Bäbler, Fribourg (CH); Jürg Burri, Sutz (CH); Hans Felber, Hergiswil (CH); Urs Buntschu, Port (CH); Werner Salvisberg, Lyss (CH)

(73) Assignee: Saphirwerk Industrieprodukte AG, Brugg (CH)

( * ) Notice: Subject to any disclaimer, the term of this patent is extended or adjusted under 35 U.S.C. 154(b) by 0 days.

(21) Appl. No.: 10/775,344

(22) Filed: Feb. 11, 2004

(65) Prior Publication Data

US 2004/0226343 A1 Nov. 18, 2004

(30) Foreign Application Priority Data

Feb. 20, 2003 (EP) .......................................... 03075495

(51) Int. Cl.$^7$ ................................................. G01N 3/08
(52) U.S. Cl. ........................................................ 73/824
(58) Field of Search .................................. 73/818, 824

(56) References Cited

U.S. PATENT DOCUMENTS

| | | | | |
|---|---|---|---|---|
| 5,259,249 A | * | 11/1993 | Fetto ........................... | 73/794 |
| 5,649,779 A | * | 7/1997 | Martin et al. .................. | 403/51 |
| 6,176,140 B1 | | 1/2001 | Autenrieth et al. | |
| 6,564,647 B1 | * | 5/2003 | Richter et al. ................ | 73/818 |

FOREIGN PATENT DOCUMENTS

| | | | | |
|---|---|---|---|---|
| DE | 2728007 | * | 8/1978 | ............. A61F/1/00 |
| DE | 44 11 508 A1 | | 10/1995 | |
| WO | WO 00/16066 | | 3/2000 | |

OTHER PUBLICATIONS

European Search Report, completed Aug. 14, 2003, by C–F Korth, Berlin.

* cited by examiner

Primary Examiner—Hezron Williams
Assistant Examiner—John Fitzgerald
(74) Attorney, Agent, or Firm—Griffin & Szipl, P.C.

(57) ABSTRACT

The invention concerns a device for testing, in a destructive or non-destructive manner, femoral head prosthesis having a blind hole for receiving the end of a femoral prosthesis rod. The device includes a frame provided with a shaft projecting from the frame, said shaft having a substantially complementary shape to said bore and being associated with means for applying a pressure onto the inner bore wall when a femoral head is fitted onto said shaft.

This device is characterised in that the shaft includes a sealed jacket having at least one deformable lateral wall portion, and a socket fitted onto said jacket and provided with elastic fingers that extend substantially facing said deformable wall portion of the jacket, and in that said jacket defines an inner chamber in communication with means supplying a pressurized fluid, such that the fluid pressure is transmitted to the inner bore wall via the deformable wall and the elastic fingers.

12 Claims, 3 Drawing Sheets

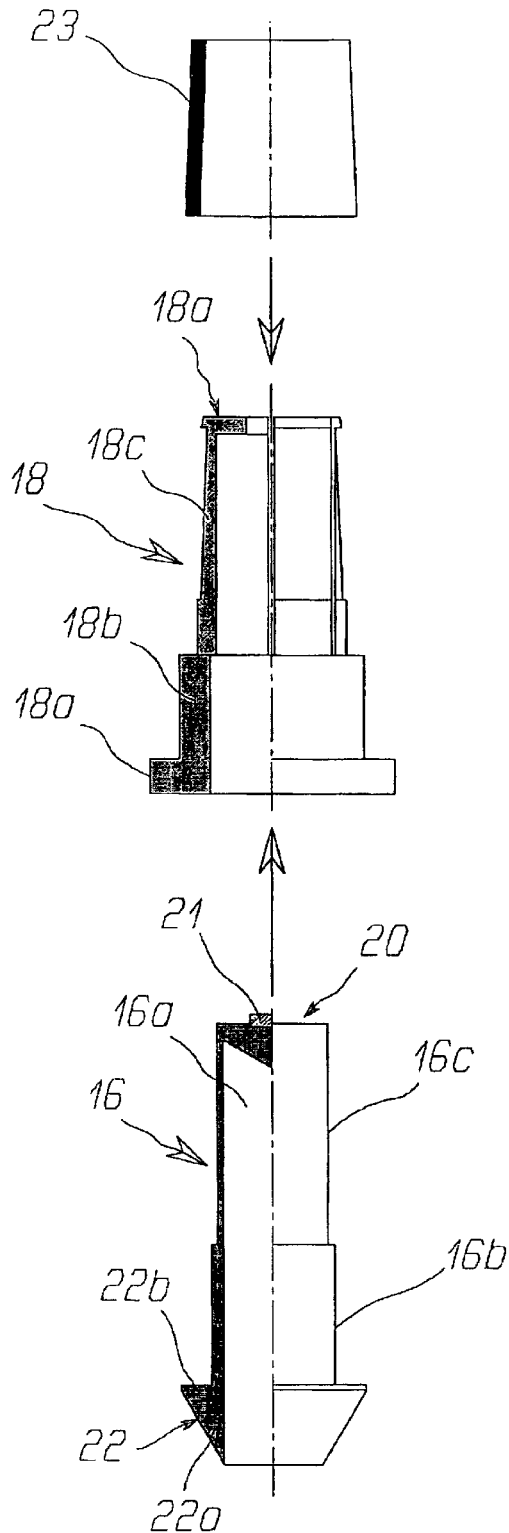
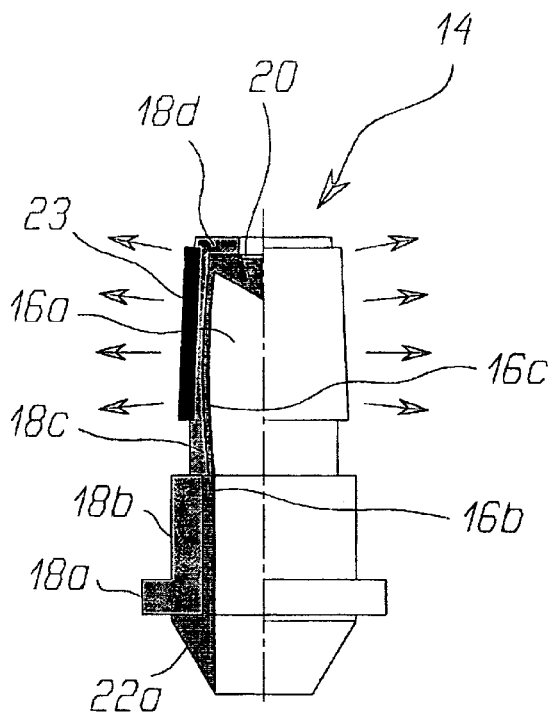
Fig. 3
Fig. 4
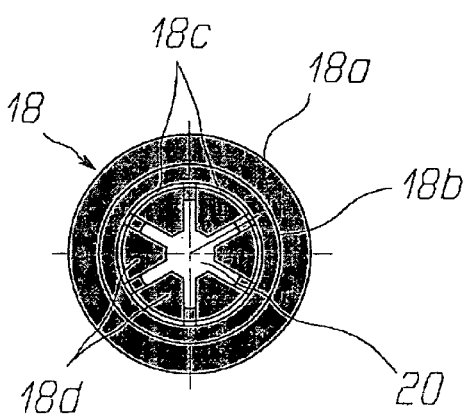
Fig. 5

TEST DEVICE FOR FEMORAL HEAD PROSTHESIS

This application claims priority from European Patent Application No. 03075495.6, filed Feb. 20, 2003, the entire disclosure of which is incorporated herein by reference.

FIELD OF THE INVENTION

The present invention concerns a device for testing femoral head prosthesis, in particular for testing femoral head prosthesis made of ceramic material.

BACKGROUND OF THE INVENTION

In a known manner, femoral prosthesis include a femoral rod for implanting in the medullary cavity. The rod ends in a truncated end portion and is covered by fitting a femoral head having the general shape of a sphere. The ball is provided with a blind bore and has a complementary shape to that of the end portion of the femoral rod. These balls, which are most often made of ceramic material, for example $ZrO_2$, $Al2O3$, $Si_3N_4$, etc., are subjected during use to high mechanical stresses and must consequently answer elevated reliability criteria.

Despite the great care taken during the manufacture of such heads, they inevitably include microscopic defects. These heads consequently have to be tested at the end of manufacture in order to eliminate those with defects exceeding a critical size. In order to do this, several tests have been envisaged.

A first test, called the "Proof test" consists in applying a regular force over the inner surface of the truncated bore of the ball, the force applied being considerably less than the maximum force causing the ball to break. By way of example, this test imposed by the American Food and Drug Administration recommends that the femoral heads to be implanted pass this test and, in particular, resist a minimum force of 20 kN.

This test is generally implemented in an apparatus of the type illustrated schematically in FIG. 1. This apparatus includes a truncated shaft 1 projecting from a base 2. Shaft 1 includes flow channels 4 for a pressurized fluid, opening out onto its truncated surface. The shaft is covered by a sleeve 6 made of plastic material. Sleeve 6 includes in its inner part an annular groove 8, which, with the truncated surface of the shaft defines a pressure chamber in which the pressurized fluid flows. At the location of groove 8, the wall of sleeve 6 is thinned and forms a deformable membrane that can abut against the inner wall of the bore. The femoral head test is carried out in the following manner. The head is fitted onto the shaft and is held in this position by a counter-support. A pressurized fluid is then introduced into the flow channels arranged in the shaft to generate the desired pressure on the lateral wall of the bore. The pressure is transmitted via the deformable membrane of the sleeve. By way of indication, the pressure necessary for implementing the Proof test on this type of apparatus are of the order of 650 bars.

A second test implemented by the manufacturers of femoral heads consists in taking samples from the manufacturing batches and subjecting them to a destructive test aimed at determining the mean breakage resistance per batch, for example as a function of the shape of the truncated housing, the quality of the ceramic material, the roughness of the surface and the micro-cracks caused by the manufacturing process.

The test apparatus described hereinbefore does not allow sufficiently high pressures to be used to determine the maximum pressure at which the ball breaks, since the sleeve made of plastic material does not resist such pressure, which can exceed 5000 bars. It is thus necessary to use another apparatus to carry out these tests. The apparatus used for this includes a shaft provided with a truncated end onto which the femoral head is fitted. The shaft is mobile in translation along its longitudinal axis and can be pushed into the head to apply a force by wedge effect on the lateral wall of the bore while it is held by a counter-support, until the head breaks. The breaking force is recorded and thus provides statistical data allowing the heads of a batch to be characterized and the end quality of the heads to be checked.

Unfortunately, this apparatus cannot be used to implement the Proof test. Indeed, when this test is implemented, metal particles from the friction of the shaft on the inner wall of the bore of the heads are deposited on the wall and make the heads unusable for the desired medical application.

Moreover, the conical part of the shaft is deformed during the test and has to be regularly replaced, typically every two or three tests. Another drawback of this apparatus arises from the very nature of the test, in that the wedge effect used does not allow uniform pressure to be applied over the entire periphery of the inner wall of the bore and inevitably leads to concentrations of stress in certain areas of the head because of surface defaults or other imperfections. These concentrations of stress increase the dispersion of the break load values and thus prejudice the statistical results obtained.

This situation means that the ceramic femoral head manufacturers have to have a test apparatus of each of the aforementioned types, which is impractical, expensive and requires significant handling of parts.

There thus exists in this field an unsatisfied demand for a device for implementing both the Proof test and the break test.

It is thus a main object of the invention to overcome the drawbacks of the aforementioned prior art, by providing a test device having a simple and economical construction and allowing both of the aforementioned tests to be implemented.

SUMMARY OF THE INVENTION

The invention therefore concerns a device for testing femoral head prosthesis having a blind bore for receiving the end of a femoral prosthesis rod, said device including a frame provided with a shaft projecting from the frame, said shaft having a substantially complementary shape to said bore and being associated with means for applying a pressure onto the inner wall of the bore when a femoral head is fitted onto said shaft, the device being characterised in that the shaft includes a sealed jacket having at least one deformable lateral wall portion, and a socket fitted onto said jacket and provided with elastic fingers which extend substantially facing said deformable wall portion of the jacket, and in that said jacket defines an inner chamber communicating with means supplying a pressurized fluid such that the fluid pressure is transmitted to the inner bore wall via said deformable wall and said elastic fingers.

Thus, simply by adjusting the hydrostatic pressure in the sealed chamber of the jacket, this test device allows both the Proof test, which requires implementing low pressures, and the break test, which requires implementing considerably higher pressures, to be carried out. It should be noted that no particular adaptation of the device has to be provided to carry out one or other of the tests, which makes this device a polyvalent and practical apparatus.

According to an advantageous feature of the invention, the shaft further includes a sleeve tube made of synthetic material covering the socket at least in the area of the fingers.

The use of this sleeve tube enables the socket, made of metal, to be advantageously insulated from the inner bore wall in order to prevent any deposit of metal particles on the inner bore wall when the Proof test is implemented. The use of such a sleeve tube also contributes to regular distribution of pressure over the inner bore wall.

BRIEF DESCRIPTION OF THE DRAWINGS

Other features and advantages of the present invention will appear in the following description of a preferred embodiment, given by way of non limiting example with reference to the annexed drawings, in which:

FIG. 3 shows a semi-cross section of the shaft of the test device according to the invention, said shaft being shown while the sealed lining and the socket are deformed by a pressurized fluid;

FIG. 4 is an exploded partial cross-section of the shaft of the test device according to the invention; and FIG. 5 is an end view of the shaft socket of the test device according to the invention.

DETAILED DESCRIPTION OF THE ILLUSTRATIVE EMBODIMENTS

Figure 1:
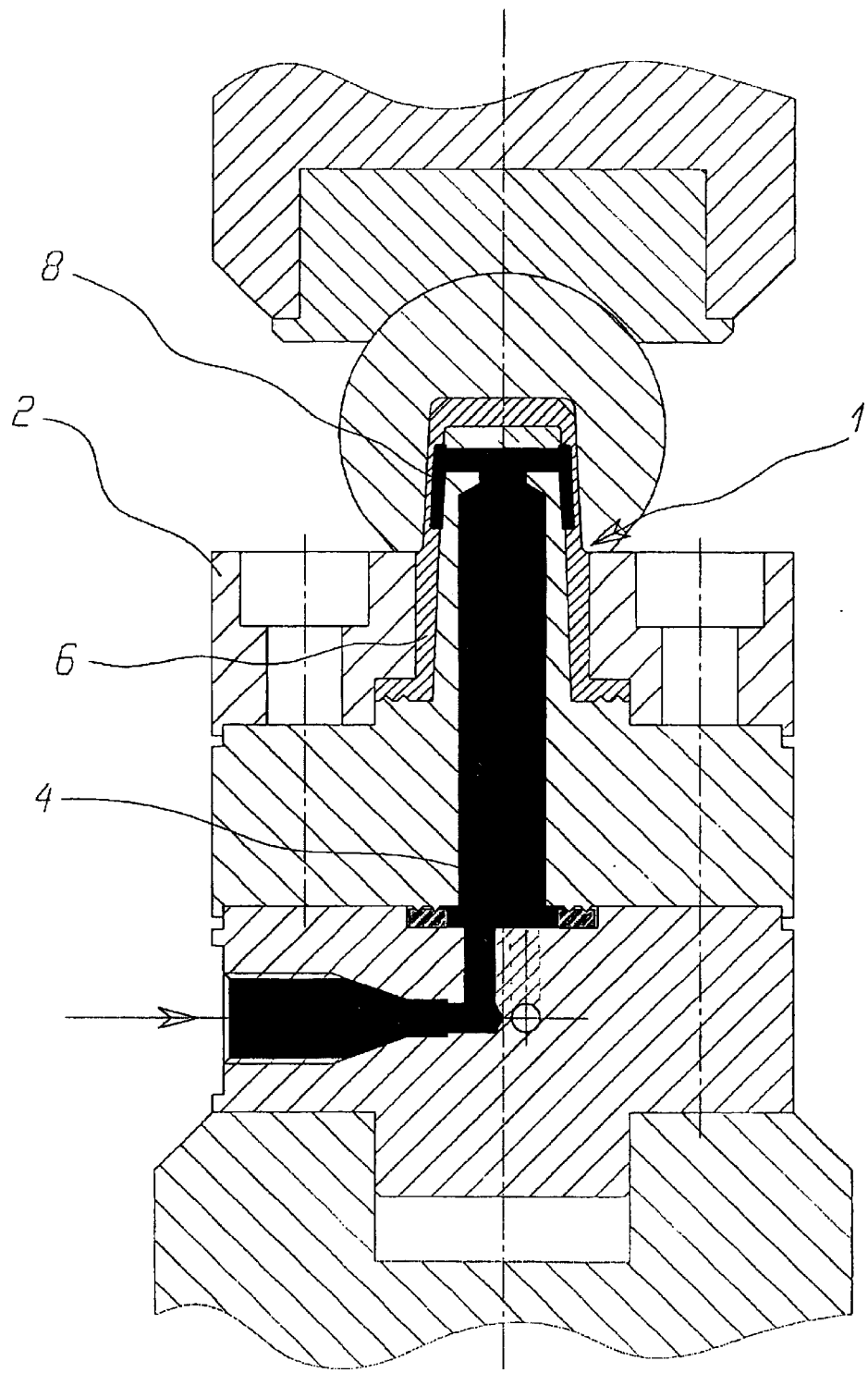
FIG. 1, already described, shows a test apparatus for femoral head prosthesis in accordance with the prior art.
Figure 2:
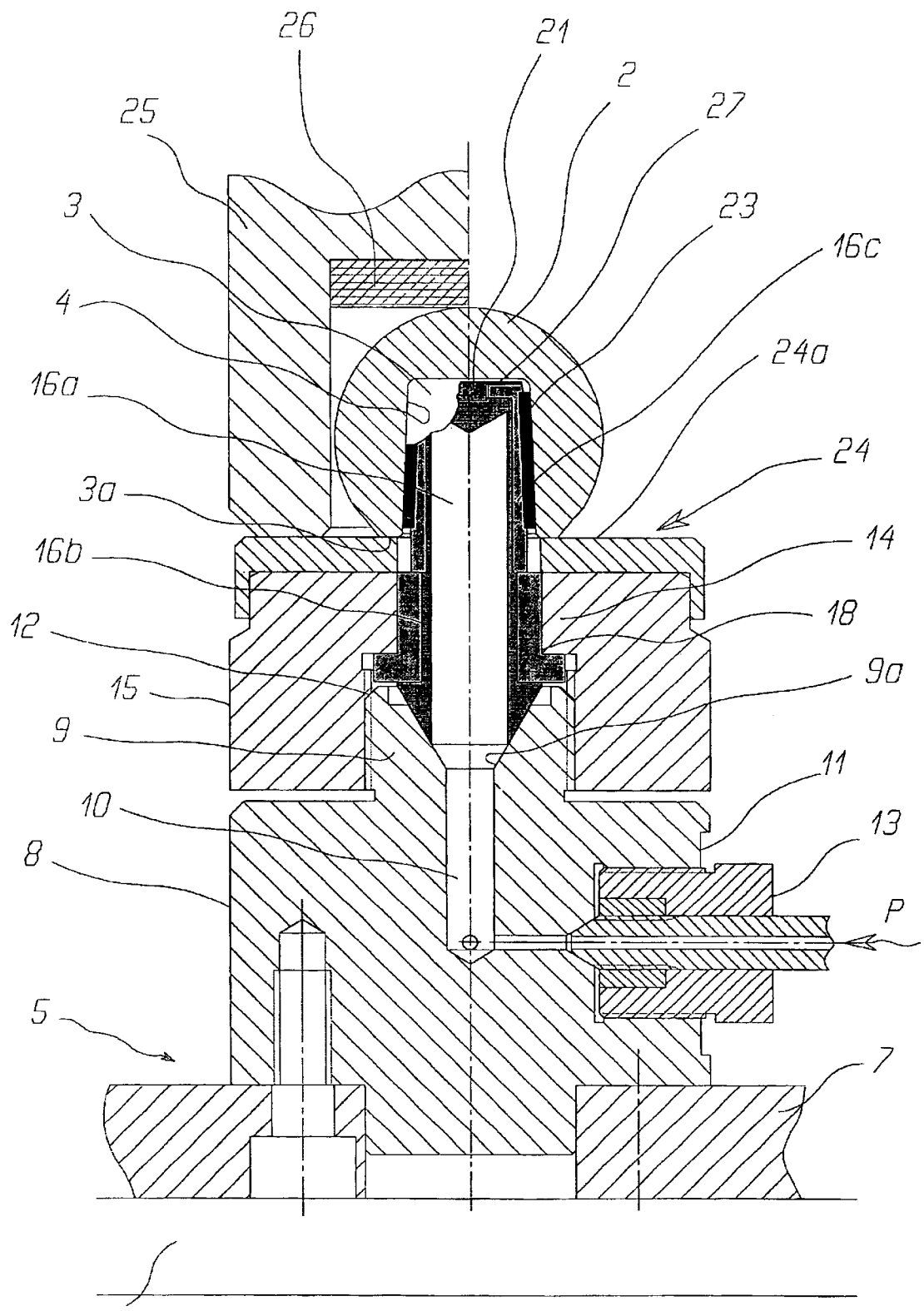
FIG. 2 shows a cross-section of a device for testing femoral head prosthesis according to the invention, the device being shown in the rest state.

FIG. 2 shows a device designated by the general reference 1 for testing femoral head prosthesis 2 according to the invention. These heads 2, which are generally made of ceramic material, for example $ZrO_2$, $Al_2O_3$, $Si_3N_4$, have the general shape of a ball provided with a blind bore 3 for receiving one end of a femoral prosthesis rod (not shown). Bore 3 usually has an inner wall 4 of truncated shape.

Test device 1 includes a frame 5 including a table 6 bearing a mounting plate 7 which in turn bears a base 8 ending in an end portion 9 provided with an external threading. Base 8 includes a channel 10, which extends from its lateral wall 11 to open out substantially into the end face 12 of end portion 9 via an orifice 9a of truncated shape. The end of channel 10 that opens out onto lateral wall 11 is connected by means of a connector 13 to a fluid pressure source P symbolised by an arrow. A shaft 14 having a substantially complementary shape to bore 3 is fixedly mounted on base 8 via a fixing nut 15 to project from frame 5.

Shaft 14 includes a sealed jacket 16 (FIGS. 3 and 4) onto which a socket 18 is fitted. Sealed jacket 16 has the general shape of a hollow cylinder closed at one end by a bottom 20 and thus defines a chamber 16a. Jacket 16 includes at its open end a shoulder 22 having a truncated first external face 22a extending from its open end, this first face 22a being extended by a second external face 22b extending perpendicularly to the longitudinal axis of the jacket. The first external face 22a is intended to rest in orifice 9a of complementary shape in order for channel 10 to communicate with the inner space of jacket 16. The fact that these two truncated surfaces rest against each other ensures the sealing of chamber 16a as regards the exterior. Jacket 16 includes, from shoulder 22 a first lateral wall portion 16b, typically cylindrical in shape, extended by a second preferably elastically deformable lateral wall portion 16c. The ability of portion 16c to be deformed is achieved by a reduction in the thickness thereof with respect to that of first wall portion 16b. Given the cylindrical shape of portion 16c, it takes the general shape of a barrel when it is deformed (FIG. 3), for example after a fluid has been pressurized in chamber 16a. It will also be noted that sealed jacket 16 includes in its upper part, in this case at bottom 20, reinforcing means for limiting the transmission of the pressure prevailing in chamber 16a towards the bottom of the bore. More precisely, these reinforcing means are integrated in bottom 20, which has, for this purpose, an overthickness with respect to the other wall portions of jacket 16. In the example illustrated, the overthickness has the shape of a pin whose tip is directed towards the inside of chamber 16a. It will be noted in this regard that bottom 20 preferably also includes, on its face directed towards the exterior, a centring stud 21 for socket 18. Stud 21 can either be formed separately from bottom 20, or can be integral with the latter. If stud 21 is a separate part from bottom 20, it will preferably be made of a synthetic material.

In order to provide an idea, the jacket can typically be made of a hardened metal such as tempered steel and the thickness of the deformable wall portion can be of the order of 0.4 mm. Such a jacket easily allows hydraulic pressures of the order of 6000 bars to be borne.

Referring also to FIG. 4, it can be seen that socket 18, fitted onto the jacket, includes an edge 18a via which it is fixedly held on jacket 16 by means of securing nut 15. The socket includes from this edge 18a, a first cylindrical portion 18b, which extends substantially around the first lateral wall portion 16b of jacket 16. Cylindrical portion 18b is then extended by a plurality of elastically deformable fingers 18c, which together define a complementary shape to that of jacket 16, in this case a cylindrical shape. More particularly, fingers 18c, which are six in number in this example, extend substantially facing deformable wall portion 16c and are preferably in intimate contact with wall portion 16c when socket 18 is fitted onto jacket 16. Thus, any deformation of the deformable wall portion of the jacket is transmitted in an optimum manner to fingers 18c of socket 18, which, in turn, are deformed separating outwards. In the example illustrated, the end of the fingers is bent inwards so as to define a substantially flat frontal face 18d (FIG. 5). It will also be noted that this frontal face 18d includes a centring orifice for cooperating with centring stud 21 (not shown in FIG. 5) of jacket 16.

FIG. 3 also shows that the shaft further includes a sleeve tube 23 made of synthetic material and covering socket 18 at least in the region of fingers 18c, this sleeve tube being elastically deformable, and that the frontal face of the socket is also covered with a disc of synthetic material 27. By way of example, the sleeve tube and the disc can be made of polyethylene. These two elements prevent any direct contact between the walls of the bore (lateral and bottom wall) with the metal elements of the shaft, which removes any problems of polluting head 2 making it impossible to use afterwards particularly for medical applications.

In an alternative embodiment, wherein the device is used to implement the head breakage test, sleeve tube 23 can be made of metal. This has the advantage of protecting fingers 18c while preventing any direct contact with the lateral bore wall at the high pressures implemented during a breakage test.

Test device 1 further includes a cupel-shaped wedge 24 pierced at its centre and fitted onto securing nut 15 so as to provide a support surface 24a having a determined height with respect to the top of shaft 14. It is thus possible to choose a wedge that, when head 2 is fitted onto shaft 14, allows the peripheral edge 3a of bore 3 to rest on support surface 24a. The cupel 24 thus forms support means for the base of femoral head 2, whose height can be adjusted with respect to shaft 14 to fit different depths of bore 3.

In order to hold head 2 in position on device 1 during tests, the device further includes counter-support means 25 for applying femoral head 2 against support surface 24a. It will be noted that these means only apply the pressure necessary to hold head 2 in position on the shaft and consequently do not have any role in the application of test pressures. Here again, in order to prevent any direct contact between the head and a metal counter-support, a plate 26 made of synthetic material, for example polyethylene, is inserted between head 2 and the counter-support.

Thus, when a femoral head 2 is fitted onto said shaft 14 and chamber 16a receives a pressurized fluid, the fluid pressure is transmitted from deformable wall 16c towards elastic fingers 18c, which in turn, by separating, transmit a pressure to inner wall 4 of bore 3 (FIG. 3).

Owing to the construction that has just been described and particularly to the structure of shaft 14 made of two metal parts, if necessary associated with a synthetic sleeve tube, it is possible to vary the pressure exerted by the shaft on the inner lateral wall of the bore within a wide range of pressure, particularly for implementing the Proof test and the breakage test.

It will be understood that various modifications and/or improvements that are obvious to those skilled in the art could be made to the embodiment described in the present description without departing from the scope of the present invention defined by the annexed claims. In particular, one could use a shaft that is not made of synthetic material, or implement the test device without the counter-support means. In the case where these counter-support means are used, one could integrate or associate various measurement sensors therewith, for example a sensor measuring the movement of the head during the test or a microphone for measuring and/or detecting noise levels resulting from the appearance or propagation of fissures inside the head during the test.

What is claimed is:

1. A device for testing femoral head prosthesis having a blind bore for receiving one end of a femoral head prosthesis, said device including a frame provided with a shaft projecting from the frame, said shaft having a substantially complementary shape to that of said bore and being associated with means for applying pressure onto said inner bore wall when a femoral head is fitted onto said shaft, wherein the shaft includes a sealed jacket having at least one deformable lateral wall portion, and a socket fitted onto said jacket and provided with elastic fingers, which extend substantially facing said deformable wall portion of the jacket, and wherein said jacket defines an inner chamber in communication with means supplying a pressurized fluid such that the fluid pressure is transmitted to the inner bore wall via said deformable wall and said elastic fingers.

2. A test device according to claim 1, wherein the sealed jacket includes in its upper part reinforcing means for limiting transmission of the pressure prevailing in said chamber towards the bottom of the bore along the longitudinal axis of said sealed jacket.

3. A test device according to claim 1, wherein the jacket is dimensioned to resist pressures of the order of 6000 bars.

4. A test device according to claim 1, wherein the jacket is made of hardened metal.

5. A test device according to claim 1, wherein the bore has a truncated shape.

6. A test device according to claim 1, further including means for supporting the base of the femoral head whose height can be adjusted with respect to the shaft in order to fit different bore depths.

7. A test device according to claim 6, further including counter-support means for applying the femoral head against said support means.

8. A test device according to claim 1, wherein the shaft further includes a sleeve tube covering said socket at least in the region of the fingers.

9. A test device according to claim 8, wherein said sleeve tube is elastically deformable.

10. A test device according to claim 9, wherein said sleeve tube is made of synthetic material.

11. A test device according to claim 10, wherein the sleeve tube is made of polyethylene.

12. A test device according to claim 9, wherein said sleeve tube is made of metal.

* * * * *